United States Patent [19]
Billig et al.

[11] Patent Number: 6,090,987
[45] Date of Patent: Jul. 18, 2000

[54] METAL-LIGAND COMPLEX CATALYZED PROCESSES

[75] Inventors: Ernst Billig, Huntington; David Robert Bryant, South Charleston; Craig Alan Beasley, Huntington; Donald Lee Morrison, Hurricane; Michael David Warholic; Kenneth Elwood Stockman, both of Charleston, all of W. Va.

[73] Assignee: Union Carbide Chemicals & Plastics Technology Corporation, Danbury, Conn.

[21] Appl. No.: 09/110,501

[22] Filed: Jul. 6, 1998

[51] Int. Cl.$^7$ ................................................. C07C 45/50
[52] U.S. Cl. ............................................ 568/454; 568/451
[58] Field of Search .................... 568/451, 454; 502/155, 162

[56] References Cited

U.S. PATENT DOCUMENTS

| | | | |
|---|---|---|---|
| Re. 31,812 | 1/1985 | Kuntz | 568/454 |
| 4,066,705 | 1/1978 | Hughes | 260/604 |
| 4,077,906 | 3/1978 | Hughes | 252/431 |
| 4,189,448 | 2/1980 | Carlock | 260/604 |
| 4,209,467 | 6/1980 | Kojima et al. | 260/340.7 |
| 4,248,802 | 2/1981 | Kuntz | 568/454 |
| 4,460,709 | 7/1984 | Kiso et al. | 518/700 |
| 4,567,306 | 1/1986 | Dennis et al. | 568/455 |
| 4,654,445 | 3/1987 | Ono et al. | 568/454 |
| 4,774,361 | 9/1988 | Maher et al. | 568/454 |
| 4,935,547 | 6/1990 | Leung et al. | 568/902.2 |
| 5,235,113 | 8/1993 | Sato et al. | 568/454 |
| 5,288,918 | 2/1994 | Maher et al. | 568/454 |
| 5,364,950 | 11/1994 | Babin et al. | 556/2 |
| 5,731,472 | 3/1998 | Leung et al. | 568/454 |

FOREIGN PATENT DOCUMENTS

| | | |
|---|---|---|
| 325446B1 | 1/1989 | European Pat. Off. . |
| 455261A1 | 6/1991 | European Pat. Off. . |
| 391680 | 3/1998 | European Pat. Off. . |
| 6262086 | 3/1993 | Japan . |

OTHER PUBLICATIONS

Kiso, Yoshihisa et al, "Novel Effect of Imidazole Compounds on a Homogeneous Ruthenium Carbonyl Catalyst in Hydrogenation of Carbon Monoxide: . . .", Journal of Organometallic Chemistry, 309 (1986) C26–C28.

Kiso, Yoshihisa et al, "1–Alkylbenzimidazoles as Unique Promoters for a Homogeneous Ruthenium Catalyst for Direct Ethylene Glyco Formation from Synthesis Gas", Journal of Organometallic Chemistry, 335 (1987) C27–C31.

Kiso, Yoshihisa, et al, "Ethylene Glycol from Synthesis Gas by Homogeneous Ruthhenium and Ruthenium–Rhodium Catalyst", The Chemical Society of Japan, Bull. Chem. Soc. Jpn., 60, 617–620 (1987).

Nomura, Kotohiro, et al, "Efficient Selective Reduction of Aromatic Nitro Compounds Affording Aromatic Amines under . . .", The Chemical Society of Japan, Bull. Chem. Soc. Jpn., 64, 2624–2628 (1991). vol. 64, No. 9.

Nomura, Kotohiro, et al, "Facile Selective Reduction of Aromatic Nitro Compounds Affording Amines Using . . .", Journal of Molecular Catalysis, 66 (1991) L1.

Ishino, Masaru et al, "Studies on Homogeneous Catalysts in C1 Chemistry", 1991.

*Primary Examiner*—Sreeni Padmanabhan
*Attorney, Agent, or Firm*—Gerald L. Coon

[57] ABSTRACT

This invention relates to a method of stabilizing a metal-organophosphorus ligand complex catalyst against deactivation in a process which comprises reacting one or more reactants in the presence of a metal-organophosphorus ligand complex catalyst and optionally free organophosphorus ligand to produce a reaction product fluid comprising one or more products, and in which at least a portion of said process is conducted under separation conditions sufficient to effect at least some deactivation of the metal-organophosphorus ligand complex catalyst, which method comprises conducting the portion of said process that occurs under separation conditions in the presence of one or more alkadienes sufficient to prevent and/or lessen deactivation of the metal-organophosphorus ligand complex catalyst.

17 Claims, 3 Drawing Sheets

Ligand F - Catalyst Activity

METAL-LIGAND COMPLEX CATALYZED PROCESSES

BRIEF SUMMARY OF THE INVENTION

1. Technical Field

This invention relates to metal-organophosphorus ligand complex catalyzed processes. More particularly this invention relates to the use of one or more alkadienes to prevent and/or lessen deactivation of the metal-organophosphorus ligand complex catalyst during separation, e.g., vaporization.

2. Background of the Invention

It is well known in the art that aldehydes may be readily produced by reacting an olefinically unsaturated compound with carbon monoxide and hydrogen in the presence of an rhodium-organophosphorus ligand complex catalyst and that preferred processes involve continuous hydroformylation and recycling of the catalyst solution such as disclosed, for example, in U.S. Pat. Nos. 4,148,830; 4,717,775 and 4,769,498. Such aldehydes have a wide range of known utility and are useful, for example, as intermediates for hydrogenation to aliphatic alcohols, for aldol condensation to produce plasticizers and for oxidation to produce aliphatic acids.

However, notwithstanding the benefits attendant with such rhodium-organophosphorus ligand complex catalyzed hydroformylation processes, stabilization of the catalyst and organophosphorus ligand remains a primary concern of the art. Obviously catalyst stability is a key issue in the employment of any catalyst. Loss of catalyst or catalytic activity due to undesirable reactions of the highly expensive rhodium catalysts can be detrimental to the production of the desired aldehyde. Likewise, when employing an organophosphite ligand during the hydroformylation process, degradation of the organophosphite ligand can lead to poisoning organophosphite compounds or inhibitors or acidic byproducts that can lower the catalytic activity of the rhodium catalyst or increase the rate of organophosphite ligand loss. Moreover, production costs of the aldehyde product obviously increase when productivity of the catalyst decreases.

Numerous methods have been proposed to maintain catalyst and/or organophosphorus ligand stability. For instance, U.S. Pat. No. 5,288,918 suggests employing a catalytic activity enhancing additive such as water and/or a weakly acidic compound; U.S. Pat. No. 5,364,950 suggests adding an epoxide to stabilize the organophosphite ligand; U.S. Pat. No. 4,774,361 suggests carrying out the vaporization separation employed to recover the aldehyde product from the catalyst in the presence of an organic polymer containing polar functional groups selected from the class consisting of amide, ketone, carbamate, urea, and carbonate radicals in order to prevent and/or lessen rhodium precipitation from solution as rhodium metal or in the form of clusters of rhodium; and U.S. Pat. No. 5,731,472 discloses that certain free heterocyclic nitrogen compounds may be employed to effectively prevent and/or lessen deactivation of metal-organopolyphosphite ligand complex catalysts that may occur over the course of time during a hydroformylation process directed to producing one or more aldehydes in which at least a portion of said hydroformylation process is conducted under harsh conditions such as exist in a vaporizer. Notwithstanding the value of the teachings of said references, the search for alternative methods and hopefully an even better and more efficient means for stabilizing the rhodium catalyst and organophosphite ligand employed remains an ongoing activity in the art.

For instance, while the suggested use of organophosphite promoted rhodium hydroformylation catalysts is well known in the art as seen, for example, by said U.S. Pat. No. 4,769,498, the activity of such catalysts has been found to decrease at a slow, but appreciable rate over the course of the continuous liquid recycle hydroformylation process.

This loss in catalytic activity of the organophosphite promoted rhodium hydroformylation catalyst is believed to be due in part to the low carbon monoxide partial pressure present during, for example, in the vaporization employed in the separation and recovery of the aldehyde product from the reaction product mixture. When using a vaporizer to facilitate separation of the aldehyde product of the process, a harsh environment of a high temperature and a low carbon monoxide partial pressure than employed during hydroformylation is created, and it has been found that when an organophosphite promoted rhodium catalyst is placed under such vaporizer conditions, it will deactivate at an accelerated pace with time. It is further believed that this deactivation is likely caused by the formation of an inactive or less active rhodium species. Such is especially evident when the carbon monoxide partial pressure is very low or absent. It has also been observed that the rhodium becomes susceptible to precipitation under prolonged exposure to such vaporizer conditions.

For instance, it is theorized that under harsh conditions such as exist in a vaporizer, the active catalyst, which under hydroformylation conditions is believed to comprise a complex of rhodium, organophosphorus ligand, carbon monoxide and hydrogen, loses at least some of its coordinated carbon monoxide, thereby providing a route for the formation of such a catalytically inactive or less active rhodium species.

Two potential routes for the formation of such an inactive or less catalytically active rhodium species, which may theoretically serve to explain the decline in catalytic activity that is experienced over the course of time of a rhodium-organophosphite ligand complex catalyzed hydroformylation process, involve the replacement of said lost carbon monoxide with an additional organophosphite ligand to form rhodium-bis(organophosphite) complexes or the formation of rhodium complex clusters that may be produced by polymerization of a rhodium-organophosphite ligand complex formed as a result of said lost carbon monoxide. Moreover such inactive or less active formed rhodium complexes may be susceptible to precipitation from solution due to their poorer solubility in the hydroformylation reaction medium than that of the active rhodium catalyst. Accordingly, a successful method for preventing and/or lessening such deactivation of the catalyst would be highly desirable to the art.

DISCLOSURE OF THE INVENTION

It has been discovered that certain alkadienes may be employed to effectively prevent and/or lessen deactivation of metal-organophosphorus ligand complex catalysts that may occur over the course of time during processes, e.g., a hydroformylation process directed to producing one or more aldehydes in which at least a portion of said hydroformylation process is conducted under harsh separation conditions such as exist in a vaporizer, for example, a continuous liquid recycle hydroformylation process in which separation of the aldehyde product from the hydroformylation reaction product fluid occurs under conditions of high temperature and/or low carbon monoxide partial pressure. This invention extends the viability of conventional superatmospheric product/catalyst separation by allowing temperatures in the separation zone of from about 10° C. to about 100° C. greater than temperatures in the reaction zone, which temperatures would be required, for example, for vaporization separation of C5s and higher products.

This invention relates to a method of stabilizing a metal-organophosphorus ligand complex catalyst against deactivation in a process which comprises reacting one or more reactants in the presence of a metal-organophosphorus ligand complex catalyst and optionally free organophosphorus ligand to produce a reaction product fluid comprising one or more products, and in which at least a portion of said process is conducted under separation conditions sufficient to effect at least some deactivation of the metal-organophosphorus ligand complex catalyst, which method comprises conducting the portion of said process that occurs under separation conditions in the presence of one or more alkadienes sufficient to prevent and/or lessen deactivation of the metal-organophosphorus ligand complex catalyst.

This invention also relates in part to a method of stabilizing a metal-organophosphorus ligand complex catalyst against deactivation in a hydroformylation process which comprises reacting one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes, and in which at least a portion of said hydroformylation process is conducted under separation conditions sufficient to effect at least some deactivation of the metal-organophosphorus ligand complex catalyst, which method comprises conducting the portion of said hydroformylation process that occurs under separation conditions in the presence of one or more alkadienes sufficient to prevent and/or lessen deactivation of the metal-organophosphorus ligand complex catalyst.

This invention further relates in part to a hydroformylation process which comprises reacting one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes, and in which at least a portion of said hydroformylation process is conducted under separation conditions sufficient to effect at least some deactivation of the metal-organophosphorus ligand complex catalyst, wherein the portion of said hydroformylation process that occurs under separation conditions is conducted in the presence of one or more alkadienes sufficient to prevent and/or lessen deactivation of the metal-organophosphorus ligand complex catalyst.

This invention yet further relates to a continuous liquid recycle hydroformylation process which comprises reacting one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes, and in which at least a portion of said process is conducted under separation conditions sufficient to effect at least some deactivation of the metal-organophosphorus ligand complex catalyst, wherein the portion of said hydroformylation process that occurs under separation conditions is conducted in the presence of one or more alkadienes sufficient to prevent and/or lessen deactivation of the metal-organophosphorus ligand complex catalyst.

This invention also relates in part to an improved hydroformylation process which comprises (i) reacting in at least one reaction zone one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone the one or more aldehydes from said reaction product fluid, and wherein said separation is conducted at a temperature sufficiently high and/or at a carbon monoxide partial pressure sufficiently low to effect at least some deactivation of the metal-organophosphorus ligand complex catalyst, the improvement comprising conducting said separation in the presence of one or more alkadienes sufficient to prevent and/or lessen deactivation of the metal-organophosphorus ligand complex catalyst.

This invention further relates to an improved continuous liquid recycle hydroformylation process which comprises (i) reacting in at least one reaction zone one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone the one or more aldehydes from said reaction product fluid, and wherein said separation is conducted at a temperature sufficiently high and/or a carbon monoxide partial pressure sufficiently low to effect at least some deactivation of the metal-organophosphorus ligand complex catalyst, the improvement comprising conducting said separation in the presence of one or more alkadienes sufficient to prevent and/or lessen deactivation of the metal-organophosphorus ligand complex catalyst.

DETAILED DESCRIPTION

Figure 1:
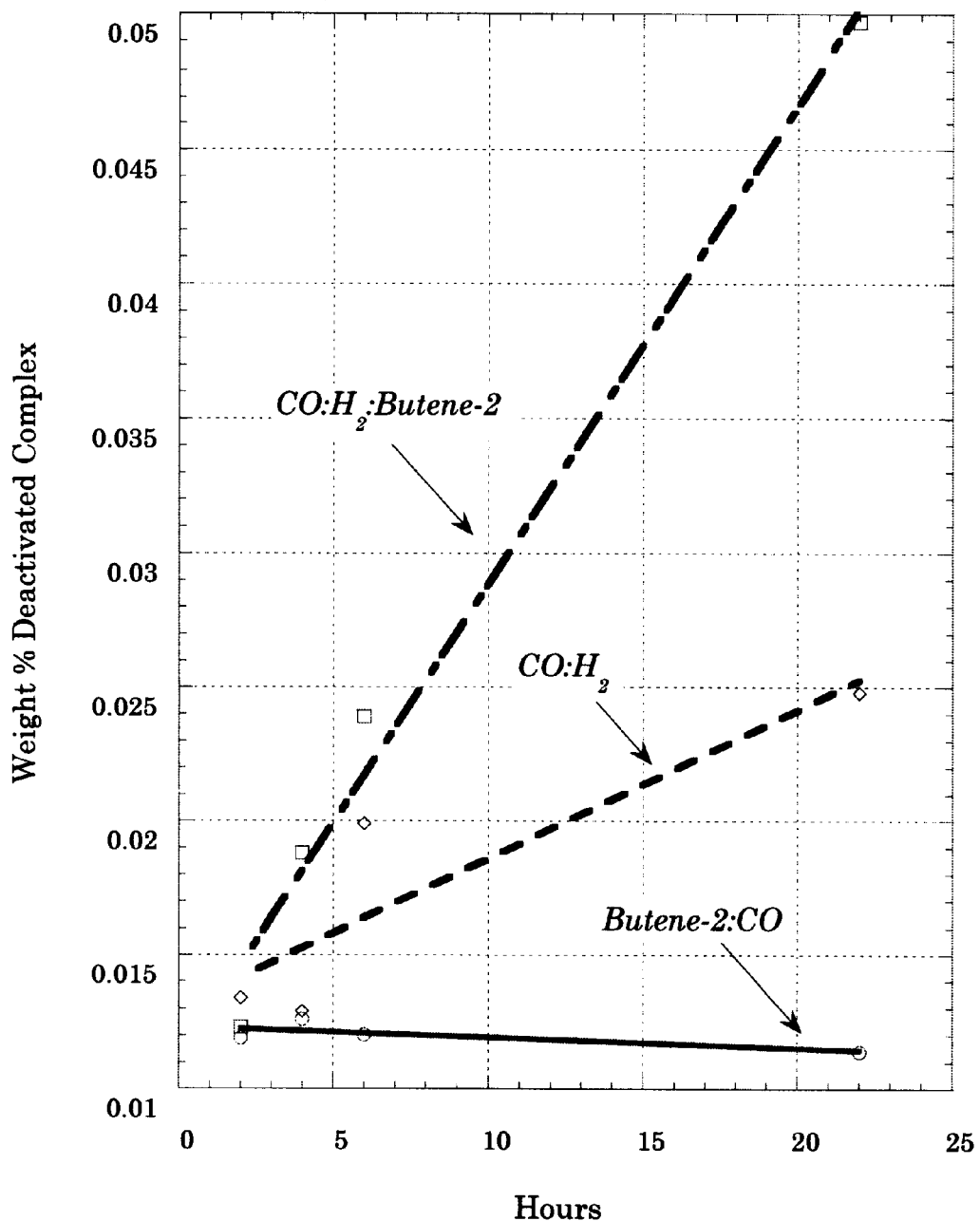
FIG. 1 depicts the results of C5 deactivated complex formation at 100° C. No deactivated complex was formed after 22 hours under butene-2 and CO. The most rapid formation of deactivated complex was under all three reactant gases. Syngas suppressed deactivated complex somewhat. See Example 1 below.

The hydroformylation processes of this invention may be asymmetric or non-asymmetric, the preferred processes being non-asymmetric, and may be conducted in any continuous or semi-continuous fashion and may involve any catalyst liquid and/or gas recycle operation desired. Thus it should be clear that the particular hydroformylation process for producing such aldehydes from an olefinic unsaturated compound, as well as the reaction conditions and ingredients of the hydroformylation process are not critical features of this invention. As used herein, the term "hydroformylation" is contemplated to include, but not limited to, all permissible asymmetric and non-asymmetric hydroformylation processes which involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. As used herein, the term "reaction product fluid" is contemplated to include, but not limited to, a reaction mixture containing an amount of any one or more of the following: (a) a metal-organophosphorus ligand complex catalyst, (b) free organophosphorus ligand, (c) one or more phosphorus acidic compounds formed in the reaction, (d) aldehyde product formed in the reaction, (e) unreacted reactants, and (f) an organic solubilizing agent for said metal-organophosphorus ligand complex catalyst and said free organophosphorus ligand. The reaction product fluid encompasses, but is not limited to, (a) the reaction medium in the reaction zone, (b) the reaction medium stream on its way to the separation zone, (c) the reaction medium in the separation zone, (d) the recycle stream between the separation zone and the reaction zone, (e) the reaction medium withdrawn from the reaction zone or separation zone for treatment in the acid removal zone, (f) the withdrawn reaction medium treated in the acid removal zone, (g) the treated reaction medium returned to the reaction zone or separation zone, and (h) reaction medium in external coolers.

Illustrative metal-organophosphorus ligand complex catalyzed hydroformylation processes which may experience such hydrolytic degradation of organophosphite ligands and catalytic deactivation include such processes as described, for example, in U.S. Pat. Nos. 4,148,830; 4,593,127; 4,769, 498; 4,717,775; 4,774,361; 4,885,401; 5,264,616; 5,288, 918; 5,360,938; 5,364,950; and 5,491,266; the disclosures of which are incorporated herein by reference. Accordingly, the hydroformylation processing techniques of this invention may correspond to any known permissible processing techniques. Preferred processes are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organophosphorus ligand complex catalyst in a liquid medium that also contains an organic solvent for the catalyst and ligand. Preferably free organophosphorus ligand is also present in the liquid hydroformylation reaction medium. By "free organophosphorus ligand" is meant organophosphorus ligand that is not complexed with (tied to or bound to) the metal, e.g., metal atom, of the complex catalyst. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom by use of a composite membrane such as disclosed in U.S. Pat. No. 5,430,194 and copending U.S. patent application Ser. No. 08/430,790, filed May 5, 1995, the disclosures of which are incorporated herein by reference, or by the more conventional and preferred method of distilling it (i.e., vaporization separation) in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syn gas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction product fluids employable herein includes any fluid derived from any corresponding hydroformylation process that contains at least some amount of four different main ingredients or components, i.e., the aldehyde product, a metal-organophosphorus ligand complex catalyst, free organophosphorus ligand and an organic solubilizing agent for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent type materials or hydrocarbon additives, if employed.

Illustrative metal-organophosphorus ligand complex catalysts employable in such hydroformylation reactions encompassed by this invention as well as methods for their preparation are well known in the art and include those disclosed in the above mentioned patents. In general such catalysts may be preformed or formed in situ as described in such references and consist essentially of metal in complex combination with an organophosphorus ligand. It is believed that carbon monoxide is also present and complexed with the metal in the active species. The active species may also contain hydrogen directly bonded to the metal.

The catalyst useful in the processes includes a metal-organophosphorus ligand complex catalyst which can be optically active or non-optically active. The permissible metals which make up the metal-organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include organophosphines, e.g., triorganophosphines, and organophosphites, e.g., mono-, di-, tri- and polyorganophosphites. Other permissible organophosphorus ligands include, for example, organophosphonites, organophosphinites, organophosphorus amides and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory or mechanistic discourse; it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2$=$CHCH_2$, $CH_3CH$=$CHCH_2$, $C_6H_5CN$, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphines and organophosphites that may serve as the ligand of the metal-organophosphorus ligand complex catalyst and/or free ligand of the processes of this invention may be of the achiral (optically inactive) or chiral (optically active) type and are well known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphines and organophosphites are preferred.

Among the organophosphines that may serve as the ligand of the metal-organophosphine complex catalyst and/or free organophosphine ligand of the reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl bisphosphines and bisphosphine mono oxides, and the like. Of course any of the hydrocarbon radicals of such tertiary non-ionic organophosphines may be substituted if desired, with any suitable substituent that does not unduly adversely affect the desired result of the hydroformylation reaction. The organophosphine ligands employable in the reactions and/or methods for their preparation are known in the art.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, for example, alkyl radicals, alkoxy radicals, silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$OC(O)R^2$; amido radicals such as —$C(O)N(R^2)_2$ and —$N(R^2)C(O)R^2$; sulfonyl radicals such as —$SO_2R^2$; ether radicals such as —$OR^2$; sulfinyl radicals such as —$SOR^2$; sulfenyl radicals such as —$SR^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —$N(R^2)_2$, each $R^2$ taken together can also represent a divalent bridging group that forms a heterocyclic radical with the nitrogen atom and in amido substituents such as $C(O)N(R^2)_2$ and —$N(R^2)C(O)R^2$ each —$R^2$ bonded to N can also be hydrogen. Illustrative alkyl radicals include, for example, methyl, ethyl, propyl, butyl and the like. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, for example, triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine as well as the alkali and alkaline earth metal salts of sulfonated triphenylphosphines, for example, of (tri-m-sulfophenyl)phosphine and of (m-sulfophenyl) diphenyl-phosphine and the like.

More particularly, illustrative metal-organophosphine complex catalysts and illustrative free organophosphine ligands include, for example, those disclosed in U.S. Pat. Nos. 3,527,809; 4,148,830; 4,247,486; 4,283,562; 4,400, 548; 4,482,749 and 4,861,918, the disclosures of which are incorporated herein by reference.

Among the organophosphites that may serve as the ligand of the metal-organophosphite complex catalyst and/or free organophosphite ligand of the reaction mixture starting materials are mono-organophosphites, diorganophosphites, triorganophosphites and organopolyphosphites. The organophosphite ligands employable in this invention and/or methods for their preparation are known in the art.

Representative mono-organophosphites may include those having the formula:

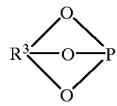

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

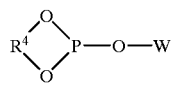

(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, for example, alkylene, alkylene-oxyalkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, for example, in U.S. Pat. Nos. 4,599,206 and 4,717,775, and the like, the disclosures of which are incorporated herein by reference.

Representative of a more preferred class of diorganophosphites are those of the formula:

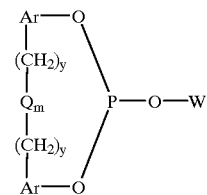

(IV)

wherein W is as defined above, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^6-$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

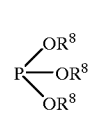

(V)

wherein each $R^8$ is the same or different and is a substituted or unsubstituted monovalent hydrocarbon radical e.g., an alkyl, cycloalkyl, aryl, alkaryl and aralkyl radicals which may contain from 1 to 24 carbon atoms. Suitable hydrocarbon radicals may contain from 1 to 24 carbon atoms or greater and may include those described above for $R^1$ in formula (I). Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

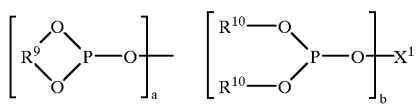
(VI)

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$—$Q_m$—$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

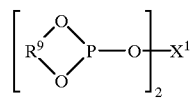
(VII)

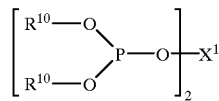
(VIII)

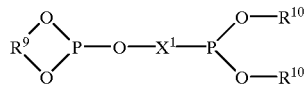
(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

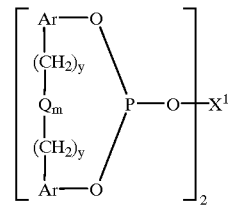
(X)

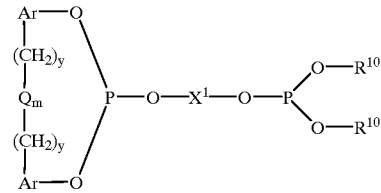
(XI)

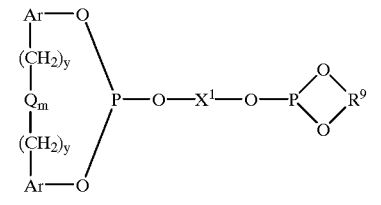
(XII)

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —C($R^5$)$_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^3$, $R^4$, $R^8$, $R^9$, $R^{10}$, $X^1$, $X^2$, W, Q and Ar radicals of such organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si($R^{12}$)$_3$; amino radicals such as —N($R^{12}$)$_2$; phosphine radicals such as -aryl-P($R^{12}$)$_2$; acyl radicals such as —C(O)$R^{12}$; acyloxy radicals such as —OC(O)$R^{12}$; amido radicals such as —CON($R^{12}$)$_2$ and —N($R^{12}$)COR$^{12}$; sulfonyl radicals such as —SO$_2$$R^{12}$; alkoxy radicals such as —OR$^{12}$;

sulfinyl radicals such as —SOR$^{12}$; sulfenyl radicals such as —SR$^{12}$; phosphonyl radicals such as —P(O)(R$^{12}$)$_2$; as well as, halogen, nitro, cyano, trifluoromethyl, hydroxy radicals, and the like, wherein each R$^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N(R$^{12}$)$_2$ each R$^{12}$ taken together can also represent a divalent bridging group that forms a heterocyclic radical with the nitrogen atom, and in amido substituents such as —C(O)N(R$^{12}$)$_2$ and —N(R$^{12}$)COR$^{12}$ each R$^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of organophosphite ligands include the following:

2-t-butyl-4-methoxyphenyl(3,3'-di-t-butyl-5,5'-dimethoxy-1,1'-biphenyl-2,2'-diyl)phosphite having the formula:

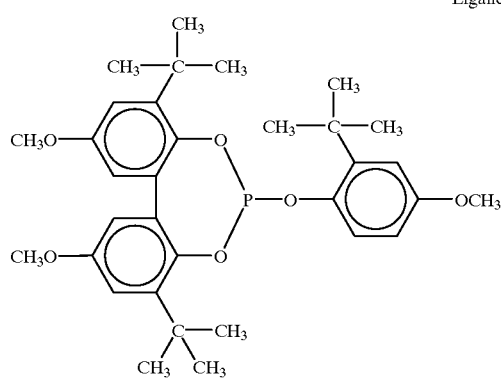

Ligand A methyl(3,3'-di-t-butyl-5,5'-dimethoxy-1,1'-biphenyl-2,2'-diyl)phosphite having the formula:

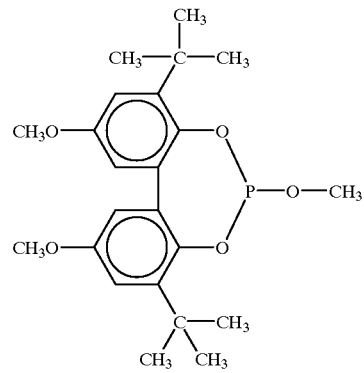

Ligand B 6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

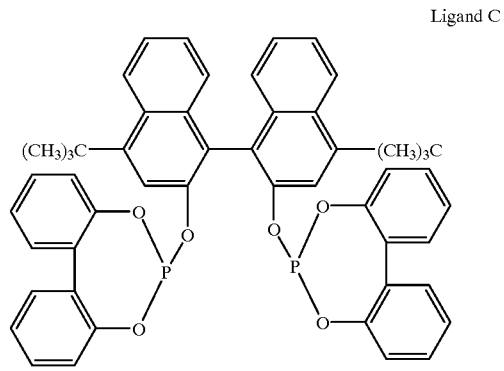

Ligand C 6,6'-[[3,3'-bis(1,1-dimethylethyl)-5,5'-dimethoxy-[1,1'-biphenyl]-2,2'-diyl]bis(oxy)]bis-dibenzo[d,f][1,3,2] dioxaphosphepin having the formula:

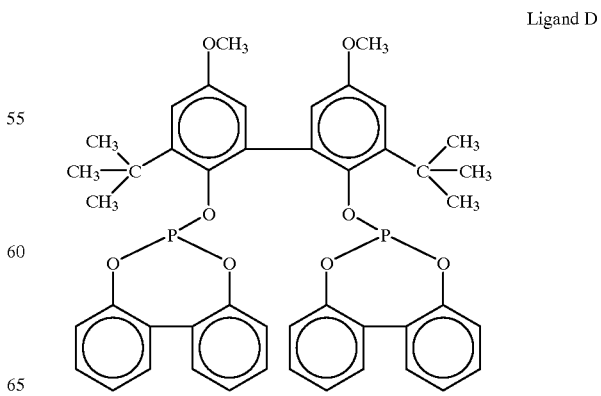

Ligand D 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

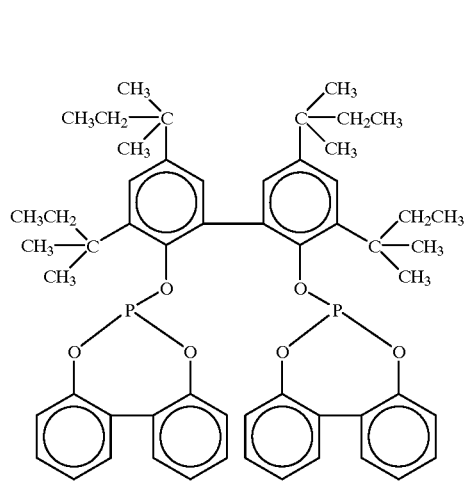

Ligand E

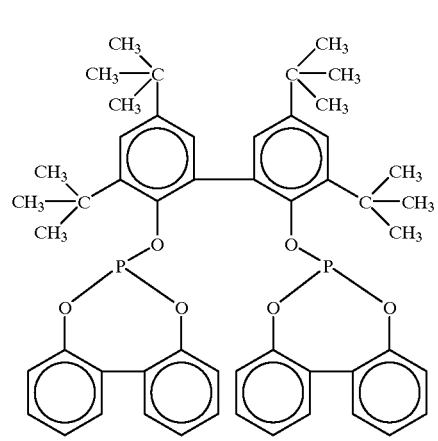

Ligand F (2R,4R)-di[2,2'-(3,3',5,5'-tetrakis-tert-amyl-1,1'-biphenyl)]-2,4-pentyldiphosphite having the formula:

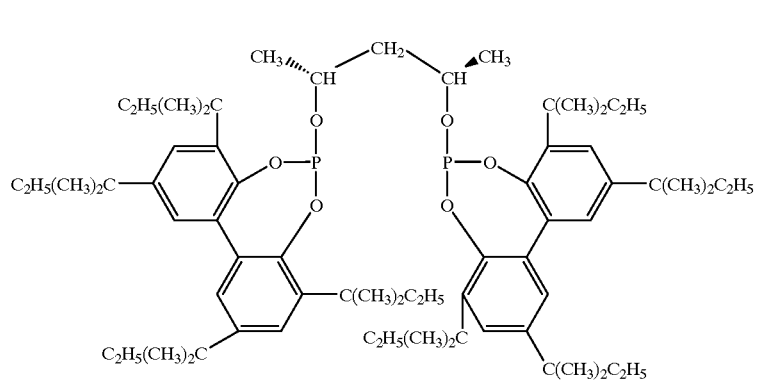

Ligand G 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

(2R,4R)-di[2,2'-(3,3',5,5'-tetrakis-tert-butyl-1,1'-biphenyl)]-2,4-pentyldiphosphite having the formula:

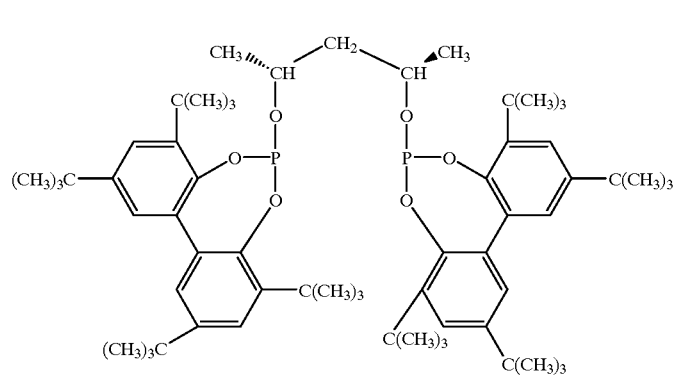

Ligand H (2R,4R)-di[2,2'-(3,3'-di-amyl-5,5'-dimethoxy-1,1'-biphenyl)]-2,4-pentyldiphosphite having the formula:
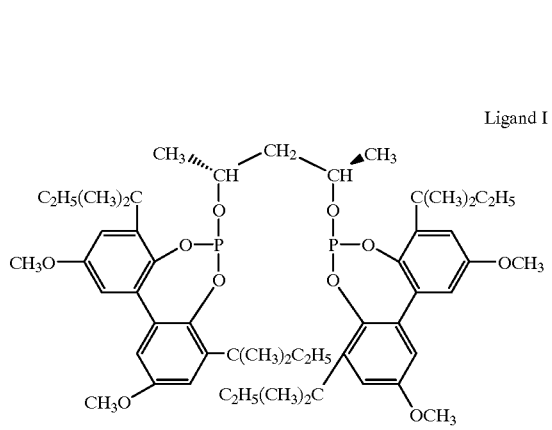
Ligand I
(2R,4R)-di[2,2'-(3,3'-di-tert-butyl-5,5'-dimethyl-1,1'-biphenyl)]-2,4-pentyldiphosphite having the formula:
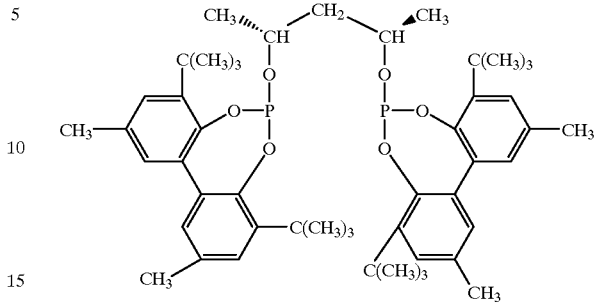
Ligand J
(2R,4R)-di[2,2'-(3,3'-di-tert-butyl-5,5'-diethoxy-1,1'-biphenyl)]-2,4-pentyldiphosphite having the formula:
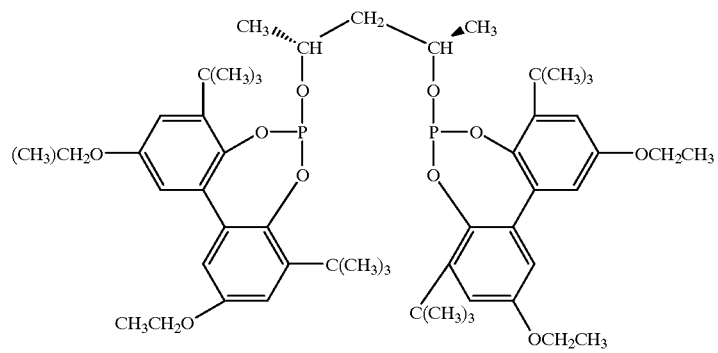
Ligand K
(2R,4R)-di[2,2'-(3,3'-di-tert-butyl-5,5'-diethyl-1,1'-biphenyl)]-2,4-pentyldiphosphite having the formula:
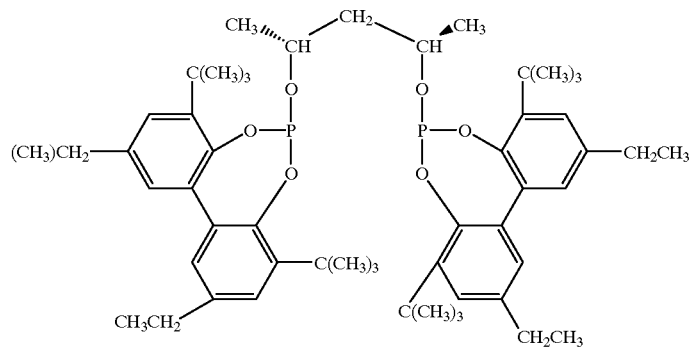
Ligand L (2R,4R)-di[2,2'-(3,3'-di-tert-butyl-5,5'-dimethoxy-1,1'-biphenyl)]-2,4-pentyldiphosphite having the formula:

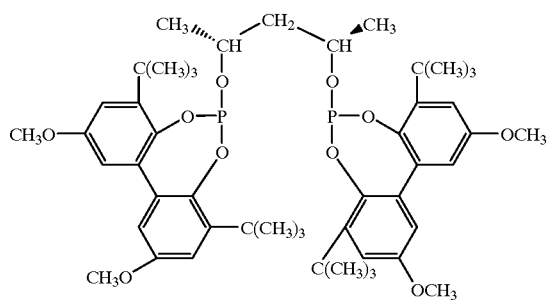
Ligand M

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

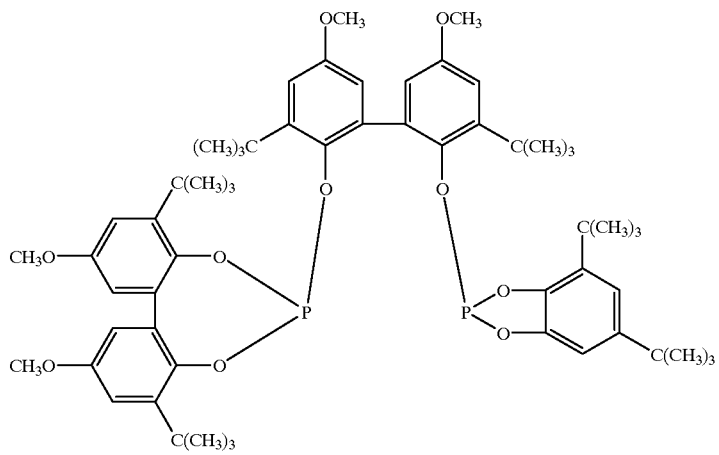
Ligand N

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

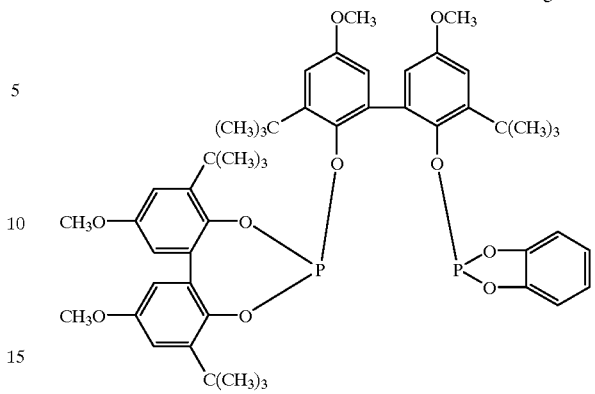
Ligand O

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

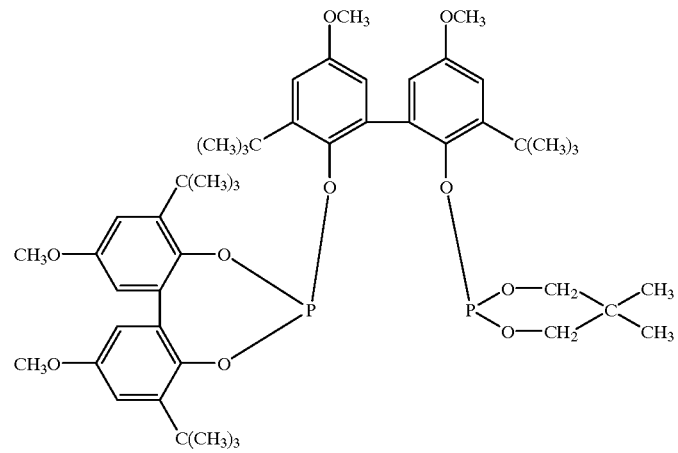
Ligand P

2'-[[4,8-bis(1,1-dimethylethyl)-2,10-dimethoxydibenzo[d,f][1,3,2]dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

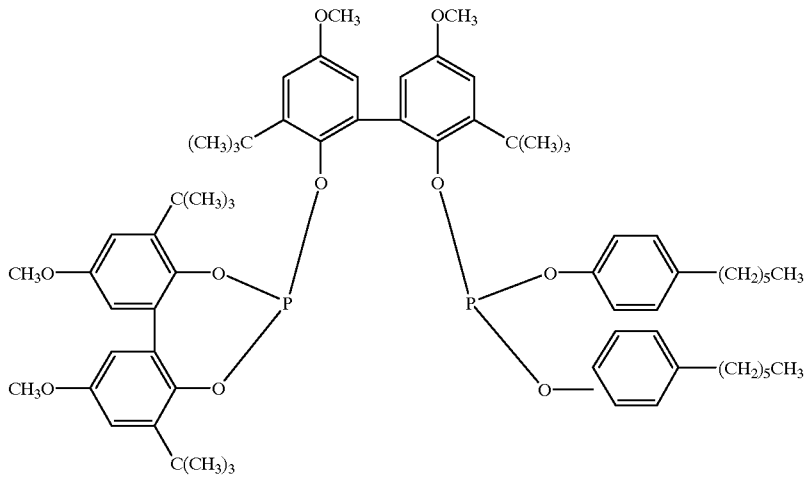

Ligand Q

2-[[2-[[4,8,-bis(1,1-dimethylethyl), 2,10-dimethoxydibenzo[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

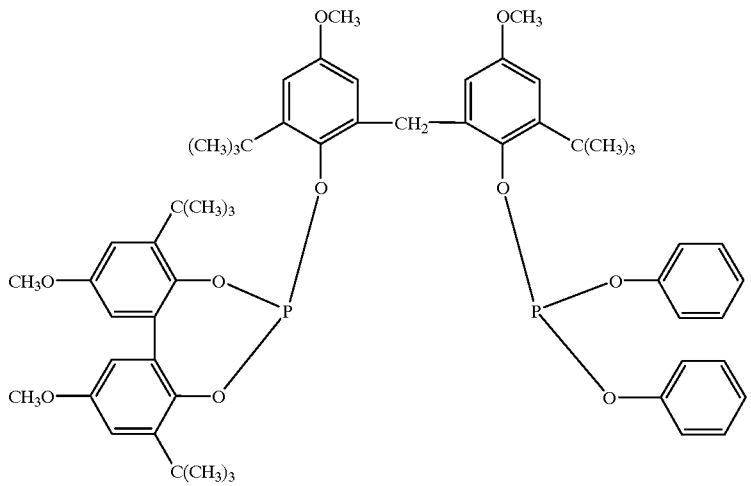

Ligand R 3-methoxy-1,3-cyclohexamethylene tetrakis[3,6-bis(1,1-dimethylethyl)-2-naphthalenyl]ester of phosphorous acid having the formula:

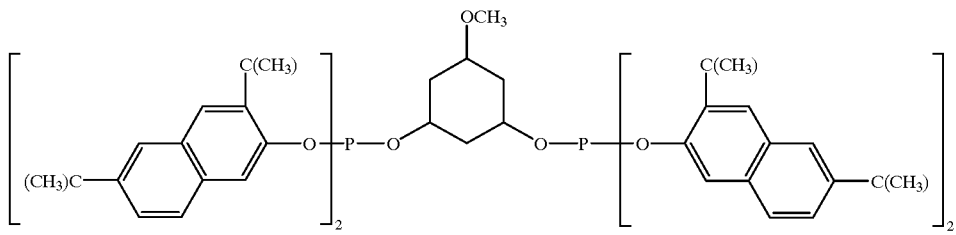
Ligand S 2,5-bis(1,1-dimethylethyl)-1,4-phenylene tetrakis[2,4-bis(1,1-dimethylethyl)phenyl]ester of phosphorous acid having the formula:

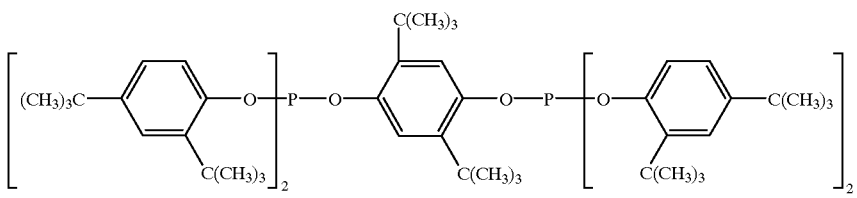
Ligand T methylenedi-2,1-phenylene tetrakis[2,4-bis(1,1-dimethylethyl)phenyl]ester of phosphorous acid having the formula:

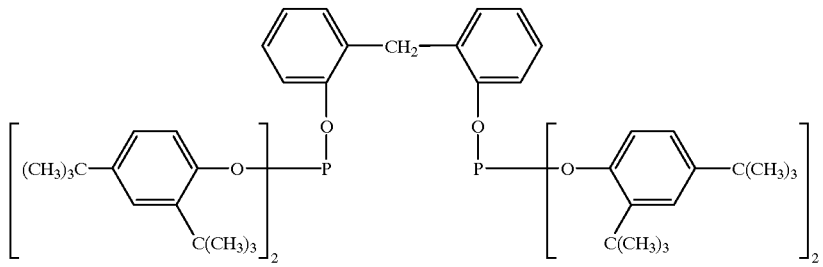
Ligand U

[1,1'-biphenyl]-2,2'-diyl tetrakis[2-(1,1-dimethylethyl)-4-methoxyphenyl]ester of phosphorous acid having the formula:

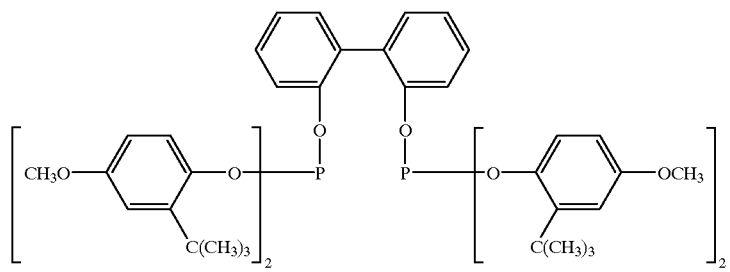
Ligand V

As noted above, the metal-organophosphorus ligand complex catalysts employable in this invention may be formed by methods known in the art. For instance, preformed rhodium hydridocarbonyl-organophosphorus ligand catalysts may be prepared and introduced into the reaction mixture of a hydroformylation process. More preferably, the rhodium-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess (free) organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-organophosphorus ligand complex precursor catalyst, an organic solvent and free organophosphorus ligand. Such precursor compositions may be prepared by forming a solution of a rhodium starting material, such as a rhodium oxide, hydride, carbonyl or salt, e.g. a nitrate, which may or may not be in complex combination with a organophosphorus ligand as defined herein. Any suitable rhodium starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial rhodium, may be complexed to the rhodium either prior to or in situ during the hydroformylation process.

By way of illustration, the preferred catalyst precursor composition of this invention consists essentially of a solubilized rhodium carbonyl organophosphorus ligand complex precursor catalyst, a solvent and optionally free organophosphorus ligand prepared by forming a solution of rhodium dicarbonyl acetylacetonate, an organic solvent and an organophosphorus ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor and hydroformylation start-up.

Accordingly, the metal-organophosphorus ligand complex catalysts used in the process of this invention consists essentially of the metal complexed with carbon monoxide and a organophosphorus ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphorus ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorus ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation processes of this invention involve the use of a metal-organophosphorus ligand complex catalyst as described herein. Of course mixtures of such catalysts can also be employed if desired. The amount of metal-organophosphorus ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 350 parts per million of metal e.g., rhodium.

In addition to the metal-organophosphorus ligand complex catalyst, free organophosphorus ligand (i.e., ligand that is not complexed with the metal) may also be present in the hydroformylation reaction medium. The free organophosphorus ligand may correspond to any of the above-defined organophosphorus ligands discussed above as employable herein. It is preferred that the free organophosphorus ligand be the same as the organophosphorus ligand of the metal-organophosphorus ligand complex catalyst employed. However, such ligands need not be the same in any given process. The hydroformylation process of this invention may involve from about 0.1 moles or less to about 100 moles or higher, of free organophosphorus ligand per mole of metal in the hydroformylation reaction medium. Preferably the hydroformylation process of this invention is carried out in the presence of from about 1 to about 50 moles of organophosphorus ligand, and more preferably for organophosphites from about 1.1 to about 4 moles of organophosphorus ligand, per mole of metal present in the reaction medium; said amounts of organophosphorus ligand being the sum of both the amount of organophosphorus ligand that is bound (complexed) to the metal present and the amount of free (non-complexed) organophosphorus ligand present. Since it is more preferred to produce non-optically active aldehydes by hydroformylating achiral olefins, the more preferred organophosphorus ligands are achiral type organophosphorus ligands, especially those encompassed by Formula (I) above, and more preferably those of Formulas (II) and (V) above. Of course, if desired, make-up or additional organophosphorus ligand can be supplied to the reaction medium of the hydroformylation process at any time and in any suitable manner, e.g. to maintain a predetermined level of free ligand in the reaction medium.

In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730. The reaction may be carried out in the slurry phase due to the high boiling points of the products, and to avoid decomposition of the product aldehydes. The catalyst may then be separated from the product mixture, for example, by filtration or decantation. In an embodiment of this invention, the metal-organophosphorus ligand complex catalyst may be slurried in the reaction product fluid.

The substituted or unsubstituted olefinic unsaturated starting material reactants that may be employed in the hydroformylation processes of this invention include both optically active (prochiral and chiral) and non-optically active (achiral) olefinic unsaturated compounds containing from 2 to 40, preferably 4 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,628,403). Moreover, such olefin compounds may further contain one or more ethylenic unsaturated groups, and of course, mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such olefinic unsaturated compounds and the corresponding aldehyde products derived therefrom may also contain one or more groups or substituents which do not unduly adversely affect the hydroformylation process or the process of this invention such as described, for example, in U.S. Pat. Nos. 3,527,809, 4,769,498 and the like.

Most preferably the subject invention is especially useful for the production of non-optically active aldehydes, by hydroformylating achiral alpha-olefins containing from 2 to 30, preferably 4 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, 2-ethyl-1-hexene, styrene, 4-methyl propylene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Prochiral and chiral olefins useful in the asymmetric hydroformylation that can be employed to produce enantiomeric aldehyde mixtures that may be encompassed by in this invention include those represented by the formula:

(VIII)

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio, acyloxy such as acetoxy; alkoxy such as methoxy and ethoxy; amino including alkylamino and dialkylamino such as benzylamino and dibenzylamino, acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360, 938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 500 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200° C. In general hydroformylation reaction temperatures of about 50° C. to about 120° C. are preferred for all types of olefinic starting materials. Of course it is to be understood that when non-optically active aldehyde products are desired, achiral type olefin starting materials and organophosphorus ligands are employed and when optically active aldehyde products are desired prochiral or chiral type olefin starting materials and organophosphorus ligands are employed. Of course, it is to be also understood that the hydroformylation reaction conditions employed will be governed by the type of aldehyde product desired.

The hydroformylation processes encompassed by this invention are also conducted in the presence of an organic solvent for the metal-organophosphorus ligand complex catalyst and free organophosphorus ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

Accordingly illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(pisobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

As indicated above, it is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorus ligand complex catalyst, and free organophosphorus ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s). Such types of recycle procedure are well known in the art and may involve the liquid recycling of the metal-organophosphorus complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In accordance with this invention, the aldehyde product mixtures may be separated from the other components of the crude reaction mixtures in which the aldehyde mixtures are produced by separation methods as described below. Suitable separation methods include, for example, solvent extraction, crystallization, distillation, vaporization, wiped film evaporation, falling film evaporation, phase separation, filtration and the like. It may be desired to remove the aldehyde products from the crude reaction mixture as they are formed through the use of trapping agents as described in published Patent Cooperation Treaty Patent Application WO 88/08835. One method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction product fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorus ligand and reaction products. When an alpha-mono-olefin reactant is also employed, the aldehyde derivative thereof can also be separated by the above methods.

More particularly, distillation and separation of the desired aldehyde product from the metal-organophosphorus complex catalyst containing reaction product fluid may take place at any suitable temperature as described below. In general, it is recommended that such distillation take place at relatively low temperatures, such as below 150° C., and more preferably at a temperature in the range of from about 50° C. to about 140° C. It is also generally recommended that such aldehyde distillation take place under reduced pressure, e.g., a total gas pressure that is substantially lower than the total gas pressure employed during hydroformylation when low boiling aldehydes (e.g., $C_4$ and below) are involved or under vacuum when high boiling aldehydes (e.g. $C_5$ and greater) are involved. For instance, a common practice is to subject the liquid reaction product medium removed from the hydroformylation reactor to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

As stated above, the subject invention resides in the discovery that metal, e.g., rhodium, catalyst deactivation as discussed herein can be minimized or prevented by carrying out separation of the desired aldehyde product from such metal-organophosphorus ligand catalyst containing product solutions in the added presence of one or more alkadienes. By the practice of this invention, the thermal stability of metal-organophosphorus ligand complex catalysts is enhanced by converting them into alkadiene complexes, i.e., by treating the reaction product fluid with an appropriate alkadiene, e.g., 1,2- or 1,3-diene, prior to exposing the reaction product fluid to separation conditions. Preferably, the alkadiene pretreatment would be carried out downstream of the reaction zone and upstream of the actual separation portion of the separation zone. The alkadiene complexes are readily converted back into fully active catalysts under hydroformylation conditions in the absence of excess alkadiene. Preferably, the alkadiene should be sufficiently volatile that the excess alkadiene required for stabilization at elevated separation temperatures, be flashed off in the separation step. The alkadiene is preferably thermally stable to polymerization and/or oligomerization at elevated temperatures. Free ligand usage is suppressed by prior alkadiene complexation.

At temperatures sufficiently high, e.g., greater than about 110° C., and/or carbon monoxide partial pressures sufficiently low, e.g., less than about 10 psi, to effect at least some deactivation of the metal-organophosphorus ligand complex catalyst, the one or more alkadienes (i) have a coordination strength with respect to the metal of said metal-organophosphorus ligand complex catalyst sufficient to effect at least some coordination with the metal of said metal-organophosphorus ligand complex catalyst, i.e., sufficient to compete with carbon monoxide to effect at least some coordination with the metal of said metal-organophosphorus ligand complex catalyst, and (ii) have a coordination strength with respect to the metal of said metal-organophosphorus ligand complex catalyst less than the organophosphorus ligand of said metal-organophosphorus ligand complex catalyst, i.e., sufficient not to compete with coordination of the organophosphorus ligand with the metal of said metal-organophosphorus ligand complex catalyst. This invention enables the use of conventional superatmospheric product/catalyst separation by allowing temperatures in the separation zone of from about 10° C. to about 100° C., preferably from about 20° C. to about 90° C., and more preferably from about 30° C. to about 80° C., greater than temperatures in the reaction zone, which temperatures would be required, for example, for vaporization separation of C5s and higher products. This invention is particularly useful in the hydroformylation of simple mono-olefin containing streams as Raffinate II where the source of the alkadiene stabilizing agents could be a slipstream of unrefined Raffinate II (containing methylacetylenepropadiene (MAPP) gas and/or butadiene) fed to the vaporizer.

Without wishing to be bound to any exact theory or mechanistic discourse it is believed that the encountered slow loss in catalytic activity of organophosphorus promoted metal hydroformylation catalysts is due at least in part to the harsh conditions such as employed in the separation and recovery of the aldehyde product from its reaction product fluid. For instance it has been found that when an organophosphorus promoted rhodium catalyst is placed under harsh conditions, e.g., high temperature and/or low carbon monoxide partial pressure, such as occur in a vaporizer, that the catalyst deactivates at an accelerated pace with time, due most likely to the formation of an inactive or less active rhodium species, which may also be susceptible to precipitation under prolonged exposure to such conditions. Such evidence is also consistent with the view that the active catalyst which under hydroformylation conditions is believed to comprise a complex of rhodium, organophosphorus ligand, carbon monoxide and hydrogen, loses at least some of its coordinated carbon monoxide ligand during harsh conditions such as exist during separation, e.g., vaporization, which provides a route for the formation of such catalytically inactive or less active rhodium species as discussed above. The means for preventing or minimizing such catalyst deactivation and/or precipitation comprises carrying out the portion of the hydroformylation process that involves harsh conditions such as the separation, e.g., vaporization, procedure of the hydroformylation process in the presence of one or more alkadienes as disclosed herein.

By way of further explanation it is believed the alkadiene serves as a replacement ligand for the lost carbon monoxide ligand thereby forming a neutral intermediate metal, e.g., rhodium, species comprising a complex of metal, organophosphorus ligand, the alkadiene and hydrogen during such separation under harsh conditions such as exist in a vaporizer, thereby preventing or minimizing the formation of any such above mentioned catalytic inactive or less active rhodium species. It is further theorized that the maintenance of catalytic activity, or the minimization of its deactivation, throughout the course of such continuous liquid recycle hydroformylation is due to regeneration of the active catalyst from said neutral intermediate rhodium species in the separation zone of the particular hydroformylation process involved. It is believed that under the higher syn gas pressure hydroformylation conditions, the active catalyst complex comprising metal, e.g., rhodium, organophosphorus ligand, carbon monoxide and hydrogen is regenerated as a result of some of the carbon monoxide in the reactant syn gas replacing the alkadiene of the neutral intermediate rhodium species. That is to say, carbon monoxide having a stronger ligand affinity for rhodium, replaces the more weakly bonded alkadiene of the neutral intermediate rhodium species that was formed during separation as mentioned above, thereby reforming the active catalyst for use in the hydroformylation reaction zone. In any event, regardless of the specific mechanism involved regarding the formation of an intermediate rhodium species and/or the regeneration of active catalyst, it should be sufficient to note, that the use of such alkadienes in accordance with this invention is considered to be excellent means for preventing or minimizing catalytic activity loss of organophosphorus promoted metal, e.g., rhodium, hydroformylation catalysts due to harsh conditions such as encountered in separation, e.g., vaporization, of the aldehyde product from its reaction production fluid.

Alkadienes useful in this invention are known materials and can be prepared by conventional processes. Alkadiene mixtures may be useful herein. The amount of alkadiene employed is not narrowly critical and can be any amount sufficient to prevent and/or lessen deactivation of the metal-organophosphorus ligand complex catalyst. Alkadienes may be fed either batchwise or continuously.

Illustrative substituted and unsubstituted alkadienes useful in this invention include, but are not limited to, conjugated aliphatic diolefins represented by the formula:

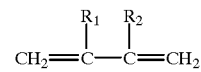

(IX)

wherein $R_1$ and $R_2$ are the same or different and are hydrogen, halogen or a substituted or unsubstituted hydrocarbon radical. The alkadienes can be linear or branched and can contain substituents (e.g., alkyl groups, halogen atoms, amino groups or silyl groups). Illustrative of suitable alkadienes are 1,3-butadiene, 2-methyl-1,3-butadiene (isoprene), dimethyl butadiene, 1,3-pentadiene (piperylene), cyclohexadiene, cyclopentadiene and cumulenes such as 1,2-propadiene (allene). For purposes of this invention, the term "alkadiene" is contemplated to include all permissible substituted and unsubstituted conjugated diolefins and cumulenes, including all permissible mixtures comprising one or more substituted or unsubstituted conjugated diolefins and/or cumulenes. Illustrative of suitable substituted and unsubstituted alkadienes (including derivatives of alkadienes) include those permissible substituted and unsubstituted alkadienes described in Kirk-Othmer, Encyclopedia of Chemical Technology, Fourth Edition, 1996, the pertinent portions of which are incorporated herein by reference.

The amount of alkadiene employable in the separation zone need only be that minimum amount necessary to furnish the basis for at least some minimization of such catalyst deactivation as might be found to occur as a result of carrying out an identical metal catalyzed hydroformylation process under essentially the same conditions, in the absence of any free alkadiene during harsh conditions such as vaporization separation of the aldehyde product. Amounts of such alkadiene ranging from about 0.01 up to about 10 weight percent, or higher if desired, based on the total weight of the hydroformylation reaction product fluid to undergo separation should be sufficient for most purposes. It is of course to be understood that as the aldehyde product is distilled from the hydroformylation product fluid, the concentration of the non-volatilized components therein, e.g. the catalyst and alkadiene, will increase accordingly. Thus the upper amount of alkadiene is governed primarily by its solubility limit in the non-volatilized liquid rhodium catalyst containing residue obtained after such separation of the aldehyde product, i.e., distillation removal of as much of the aldehyde product desired. Such amounts of the alkadiene employable herein will also depend in part upon the particular rhodium catalyst employed and the distillation temperature for recovering the aldehyde product, as well as the particular alkadiene itself. In general preferred minor amounts of the alkadiene present during the distillation of the desired aldehyde product from the metal-organophosphorus ligand complex catalyst containing product fluids of this invention may range from about 0.05 to about 5 weight percent based on the total weight of the hydroformylation reaction product fluid to be distilled.

The alkadiene should be confined to the separation zone. As used herein, "separation zone" is contemplated to include the area where the reaction product fluid is contacted with the alkadiene, the area where the product is separated from the reaction product fluid, and the area where the reaction product fluid is recycled to the reaction zone. The amount of alkadiene in the reaction zone should be minimized so as to not cause catalyst inhibition or otherwise interfere with the hydroformylation reaction (see, for example, Japan Patent Application 49215/1975). Amounts of such alkadiene in the reaction zone should in general not exceed about 1 weight percent, preferably about 0.1 weight percent, of the total weight of the hydroformylation reaction product fluid.

The addition of the alkadiene employable in this invention to the reaction product fluid from which the aldehyde product is to undergo separation may be carried out in any suitable manner desired. Preferably, the alkadiene is introduced downstream of the reaction zone and upstream of the actual spearation area of the separation zone. For instance, the alkadiene may be added to the hydroformylation reaction product fluid that has been removed from the reaction zone and at any time prior to separation of the aldehyde product therefrom. Since the alkadiene chosen to be used could have a detrimental affect on the hydroformylation reaction per se, the alkadiene should not be added directly to the hydroformylation reaction medium in the reaction zone or allowed to enter the reaction zone during the hydroformylation process in amounts sufficient to cause catalyst inhibition or otherwise interfere with the hydroformylation reaction.

The temperature of the resulting reaction product fluid/alkadiene mixture is not narrowly critical and may range, for example, from about ambient or less to about 120° C. or greater, preferably from about ambient to about 100° C., and more preferably from about 40° C. to about 80° C. The contacting time required for the reaction product fluid and alkadiene prior to entering the actual separation area of the separation zone is not narrowly critical and may range, for example, from about one second or less to about one hour or more, preferably from about 10 seconds to about 15 minutes, and more preferably from about 30 seconds to about 10 minutes.

Another problem that has been observed when organophosphite ligand promoted metal catalysts are employed in olefin hydroformylation processes that involves degradation of the organophosphite ligand and catalyst deactivation of the metal-organophosphite complex catalyzed hydroformylation processes due to the hydrolytic instability of the organophosphite ligands. A means for preventing or minimizing such catalyst deactivation and/or precipitation involves carrying out the invention described and taught in U.S. Pat. Nos. 5,741,944, 5,744,649, 5,763,671, and 5,763,677, the disclosures of which are incorporated herein by reference.

Other means for removing phosphorus acidic compounds from the reaction product fluids of this invention may be employed if desired. This invention is not intended to be limited in any manner by the permissible means for removing phosphorus acidic compounds from the reaction product fluids.

In addition to hydroformylation processes, other processes for which this invention may be useful include those which exhibit a loss in catalytic activity of organophosphite promoted metal catalysts due to harsh reaction conditions such as employed in the separation and recovery of product from its reaction product fluid. Illustrative processes include, for example, hydroacylation (intramolecular and intermolecular), hydroamidation, hydrocyanation, hydroesterification, carbonylation and the like. Preferred processes involve the reaction of organic compounds with carbon monoxide, or with carbon monoxide and a third reactant, e.g., hydrogen, or with hydrogen cyanide, in the presence of a catalytic amount of a metal-organophosphite ligand complex catalyst. The most preferred processes include hydroformylation, hydrocyanation and carbonylation. As used herein, "reaction zone" is contemplated to include the area where the above processes are carried out exclusive of the separation zone.

As with hydroformylation processes, these other processes may be asymmetric or non-asymmetric, the preferred processes being non-asymmetric, and may be conducted in any continuous or semi-continuous fashion and may involve any catalyst liquid and/or gas recycle operation desired. The particular processes for producing products from one or more reactants, as well as the reaction conditions and ingredients of the processes are not critical features of this invention. The processing techniques of this invention may correspond to any of the known processing techniques heretofore employed in conventional processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion.

The hydroformylation processes of this invention may be carried out using, for example, a fixed bed reactor, a fluid bed reactor, a continuous stirred tank reactor (CSTR), a tubular reactor, a baffled reactor, or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed in this invention may be a single vessel or may comprise two or more discrete vessels. The at least one separation zone employed in this invention may be a single vessel or may comprise two or more discrete vessels. The at least one scrubber zone employed in this invention may be a single vessel or may comprise two or more discreet vessels. It should be understood that the reaction zone(s) and separation zone(s) employed herein may exist in the same vessel or in different vessels. For example, reactive separation techniques such as reactive distillation, reactive membrane separation and the like may occur in the reaction zone(s).

The hydroformylation processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention.

EXAMPLE 1

Three glass reactors were charged with 20 milliliters each of catalyst solution containing 250 parts per million of rhodium as rhodium dicarbonyl 1,3-pentanedionate, 0.8 weight percent of Ligand F (as identified herein); 0.2 weight percent of octadecaphenone internal standard; 20 weight percent of valeraldehyde; and the balance totraethylene glycol dimethyl ether; and each placed in a 100° C. oil bath. The first reactor was kept under 5 psi each of CO and $H_2$. The second reactor was kept under 8 psi of trans-butene-2 and 6 psi each of CO and $H_2$, while the third reactor under 5 psi CO and 8 psi trans-butene-2. Each reactor was monitored at 2, 4, 6 and 24 hours for deactivated complex formation. The results are presented graphically FIG. 1. No deactivated complex was formed after 22 hours under butene-2 and CO. The most rapid formation of deactivated complex was under all three reactant gases. Syngas suppressed deactivated complex somewhat.

The $^{31}P$ NMR from the butene-2:CO treated catalyst solution indicated the presence of the allene (1,2-propadiene) inhibited form of the Ligand F catalyst, (alkadiene)Rh(Ligand F), complex II below.

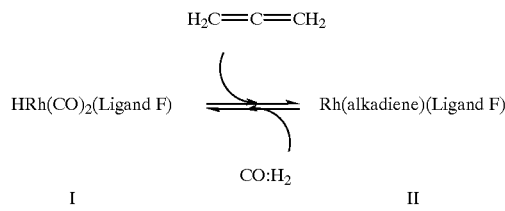

Placing the butene-2:CO treated solution under syngas, readily converted the complex II back into complex I, HRh(CO)$_2$(Ligand F), the Ligand F catalyst resting state (see above). Gas chromatographic measurements confirmed the presence of trace amounts of allene in the trans-2-butene in sufficient amounts to produce complex, II. The conversion of the Ligand F catalyst into an alkadiene complex effectively and totally suppressed deactivation at 100° C.

EXAMPLE 2

A catalyst solution (100 milliliters) was generated in a six ounce Fisher Porter Bottle by dissolving 0.063 grams of rhodium dicarbonyl 2,4-pentanedionate, 0.8 grams of Ligand F, 20 grams of n-butyraldehyde, and 78.7 grams of tetraethylene glycol dimethyl ether, subsequently alternately evacuating and flushing with nitrogen; and finally adding 60 psi of CO:$H_2$, and placing the bottles in a 100° C. oil bath for 1 hour. The resulting solution contained 200 parts per million of rhodium calculated as the metal and 0.6 weight percent of free Ligand F. The solution was cooled and alternately flushed and evacuated three times with nitrogen, then heated at 125° C. under 15 psig nitrogen for 24 hours.

About 20 milliliters of the solution was charged to a glass reactor via a syringe after purging the reactor with nitrogen (see Examples 14–20 below). After closing the reactor, the system was again purged with nitrogen and place in an oil bath heated to 100° C. The hydroformylation reaction in each experiment was conducted at a total gas pressure of 160 psig. The target partial pressure of hydrogen, carbon monoxide, and propylene being about 45 psia, 45 psia, and 5 psia respectively, with the remainder being nitrogen. The flows of the feed gases (carbon monoxide, hydrogen, propylene, and nitrogen) were controlled individually with mass flow meters. The feed gases were dispersed into the precursor solution via stainless steel 7-micron filters used as spargers. The unreacted portion of the feed gases stripped out the product aldehydes. Each experiment was operated for 24 hours under the above conditions. The average activity for each experiment is listed in Table 1 below. The activity is defined as the observed reaction rate divided by the predicted reaction rate. The reaction rates are expressed in terms of gram moles per liter per hour.

EXAMPLE 3

The same procedure as in Example 2 was followed with the exception that a slow stream of 1,2-propadiene was purged through the initially generated catalyst solution for 5 minutes. Excess was then removed by alternately evacuating and flushing with nitrogen. The resulting solution was heated at 125° C. as in Example 2, and 20 milliliters of the resulting solution was transferred to a glass reactor as in Example 2 and the activity determined. The results are given in Table 1.

EXAMPLE 4

The same procedure as in Example 3 was followed except 2 milliliters of 1,3-butadiene was added to the generated catalyst and stirred for 5 minutes. Excess 1,3-butadiene was then removed by alternate evacuation and flushing with nitrogen. The resulting solution was heated at 125° C. as in Example 2, and 20 milliliters of the resulting solution was transferred to a glass reactor as in Example 2 and the activity determined. The results are given in Table 1.

EXAMPLE 5

The same procedure as in Example 4 was followed with the exception that 50 milliliters of a catalyst solution generated as in Example 2 was treated with 0.5 milliliters of 2-methyl-1,3-butadiene (isoprene) in place of 1,3-butadiene. The results are given in Table 1.

EXAMPLE 6

The same procedure as in Example 5 was followed with the exception that 0.5 milliliters of 1,3-pentadiene (piperylene) was employed in place of 2-methyl-1,3-butadiene. The results are given in Table 1.

EXAMPLE 7

A catalyst solution (20 milliliters) was generated in a Fisher Porter Bottle as in Example 2 under 60 psi CO:H$_2$ for 1 hour, then cooled to room temperature and treated with 0.5 milliliters of 1,3-butadiene. The solution was removed from the Fisher Bottle by hypodermic syringe and transferred to a 100 milliliter stirred stainless vessel and maintained at 140° C. under 15 psi nitrogen for 14 hours. The resulting solution was then transferred to the glass reactors as in Example 2, and the residual catalyst activity measured. The results are given in Table 1.

EXAMPLE 8

The same procedure as in Example 3 was followed except the excess 1,3-butadiene was not removed and the resulting solution was heated at 140° C. for 48 hours prior to testing for residual activity in the glass reactors. The results are given in Table 1.

EXAMPLE 9

The same procedure as in Example 8 was followed except allene was employed in place of 1,3-butadiene, and the resulting solution heated at 140° C. for 48 hours without removing excess allene. The results are given in Table 1.

EXAMPLE 10

A 20 milliliter sample of freshly generated catalyst solution (prepared as in Example 2) was charged to the glass reactors and the activity measured. The results are given in Table 1.

EXAMPLE 11

The same procedure as in Example 4 was followed except Ligand D (as identified herein) was employed in place of Ligand F. The results are given in Table 1.

EXAMPLE 12

The same procedure as in Example 10 was followed except the fresh catalyst solution contained Ligand D in place of Ligand F. The results are given in Table 1.

EXAMPLE 13

The same procedure as in Example 8 was followed except 0.4 grams of 1,3-cyclohexadiene was employed in place of 1,3-butadiene. The results are given in Table 1.

TABLE 1

| Ex. # | ° C./ Time (hours) | Pretreatment Gas | Excess Diene, ✓ | Ligand | Final Rate (% Activity) |
|---|---|---|---|---|---|
| 2 | 125/24 | N$_2$ | — | F | 0.22 (10.0) |
| 3 | 125/24 | Allene | — | F | 2.22 (101) |
| 4 | 125/24 | Butadiene | — | F | 2.23 (102) |
| 5 | 125/50 | Isoprene | — | F | 1.55 (73.8) |
| 6 | 125/50 | Piperylene | — | F | 1.92 (88.1) |
| 7 | 140/14 | Butadiene | ✓ | F | 0.55 (25.2) |
| 8 | 140/48 | Butadiene | ✓ | F | 2.10 (96.3) |
| 9 | 140/48 | Allene | ✓ | F | 1.03 (47.2) |
| 10 | — | Control | — | F | 2.18 |
| 11 | 125/50 | Butadiene | ✓ | D | 1.23 (116) |
| 12 | — | Control | — | D | 1.16 |
| 13 | 140/24 | 1,3-cyclohexadiene | ✓ | F | 0.09 (4.13) |

EXAMPLES 14–16

A series of long term catalyst stability experiments were conducted in the glass reactors in a continuous propylene hydroformylation mode. The results are shown in Table 2 below. The reactor consisted of a three ounce pressure bottle submersed in an oil bath with a glass front for viewing. In each example about 20 milliliters of a freshly prepared rhodium catalytic precursor solution was charged to the reactor with a syringe after purging the system with nitrogen. Each precursor solution contained 200 parts per million of rhodium (calculated as free rhodium) introduced as rhodium dicarbonyl acetylacetonate, Ligand F and tetraglyme. The amount of Ligand F (free) employed was 0.4 weight percent.

Figure 2:
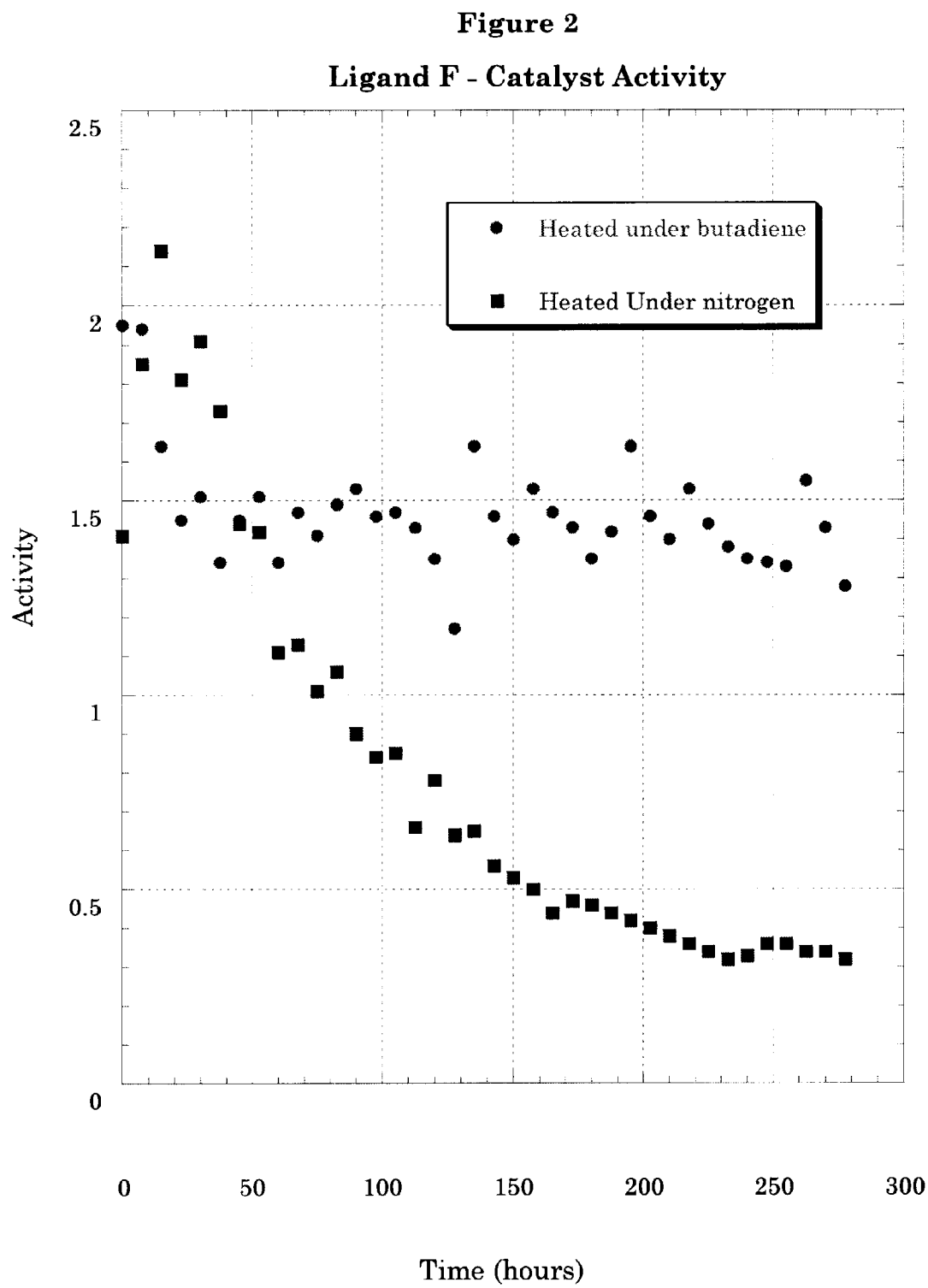
FIG. 2 depicts the results of glass reactor experiments cycling between 80° C. hydroformylation conditions and 125° C. simulated high temperature vaporizer operation in the presence of butadiene. The results demonstrate the stabilizing influence of butadiene on the catalyst. See Table 2 below.
Figure 3:
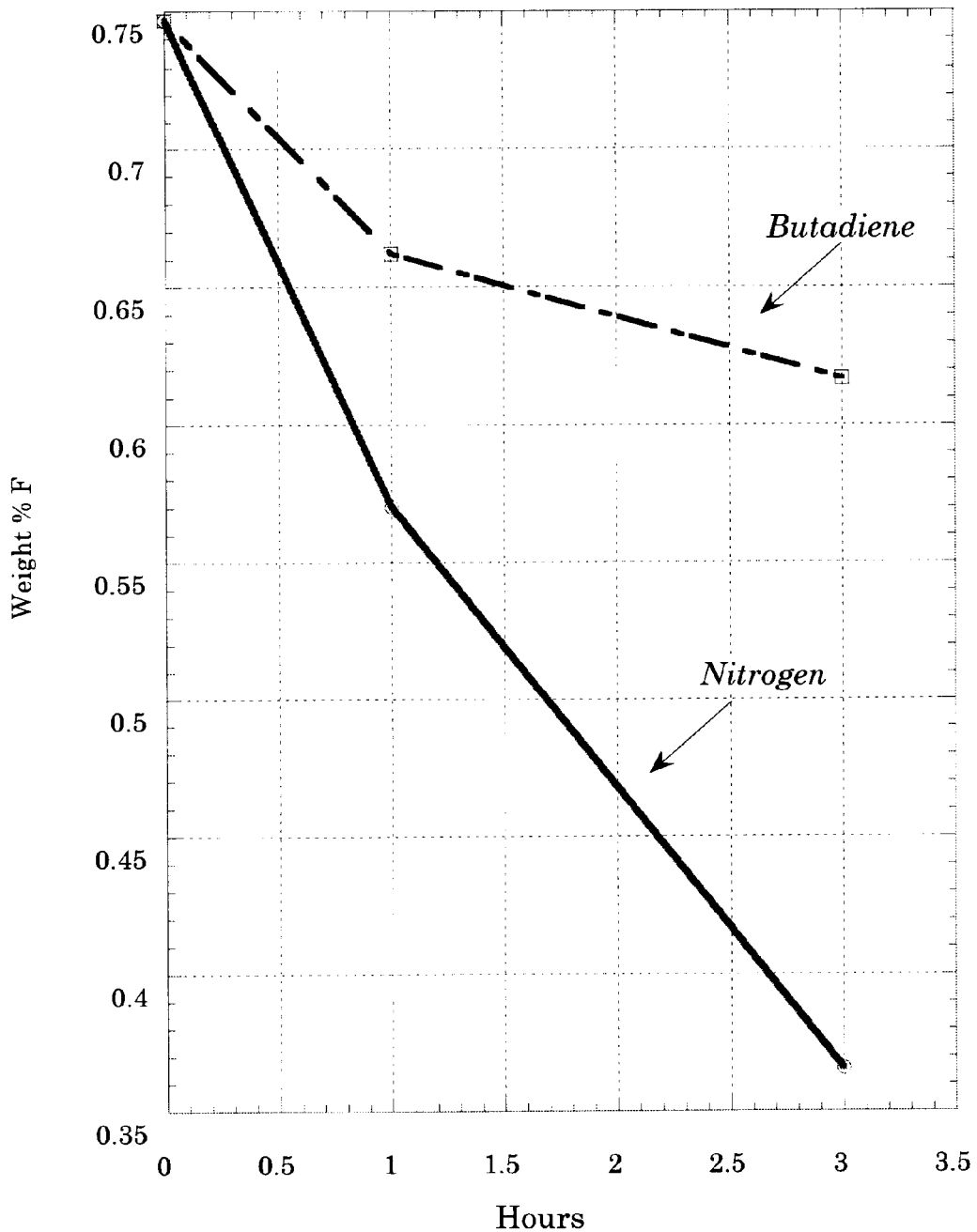
FIG. 3 depicts the results of decomposition of free Ligand F at 145° C. The results demonstrate that prior complexation of catalyst with butadiene suppresses decomposition of free Ligand F in solution. See Examples 21 and 22 below.

After closing the reactor, the system was again purged with nitrogen and the oil bath was heated to 80° C., in order to furnish the desired hydroformylation. The hydroformylation reaction in each experiment was conducted at a total gas pressure of about 165 psig, the target partial pressure pressures of hydrogen, carbon monoxide, and propylene being about 45 psia, 45 psia, and 5 psia, respectively, the remainder being nitrogen. The flows of the feed gases (carbon monoxide, hydrogen, propylene, and nitrogen) were controlled individually with mass flow meters. The feed gases were dispersed into the precursor solution via stainless steel 7-micron filters used as spargers. The unreacted portion of the feed gases stripped out the product aldehydes. Examples 14, 15 and 16 were conducted at 80° C. for 2 hours. The feed gases were then turned off and either pure nitrogen or an 88 mole percent nitrogen, 12 mole percent butadiene mixture was fed to the reactor (see Table 2). The pressure of the reactor was then let down to the appropriate pressure so that the target butadiene pressure in the reactor could be achieved. The oil bath temperature was then ramped to 125° C. over a 5 minute period. The bath remained at 125° C. for 10 minutes. The bath was then cooled to 80° C. over a 6 minute period. The nitrogen or nitrogen/butadiene mixture was then turned off and the original hydroformylation feeds (carbon monoxide, hydrogen, propylene, and nitrogen) were restarted at their original flows. This cycling process, 2 hours under hydroformylation conditions followed by 21 minutes of heated conditions, was continued for 5 days. A control catalyst solution deactivated at a rate of 8% per day at an 80° C. reactor temperature. results are given in Table 2 and FIG. 2.

EXAMPLES 17–20

Examples 17–20 were conducted in an identical manner to Examples 14–16 except the bath temperature was raised from 80° C. to 135° C. during the cycling process. A control catalyst solution deactivated at a rate of 8% day at an 80° C. reaction temperature. The results are given in Table 2.

TABLE 2

| Ex. # | Separation Temperature, ° C. | Butadiene psi | Butadiene/ Rh molar ratio | Percent Deactivation/ Day |
|---|---|---|---|---|
| 14 | 125 | 2 | 45 | 5 |
| 15 | 125 | 5 | 80 | 3 |
| 16 | 125 | $N_2$ | — | 30 |
| 17 | 135 | 2 | 55 | 5 |
| 18 | 135 | 5 | 115 | 8 |
| 19 | 135 | $N_2$ | — | 25 |
| 20 | — | Control | — | 4 |

EXAMPLE 21

A catalyst solution (5 milliliters), 600 parts per million in rhodium and 0.8 weight percent in Ligand F generated as in Example 2 was charged to a 3 ounce Fisher Porter bottle and alternately flushed evacuated with nitrogen, then placed in a 145° C. oil bath under nitrogen (80 psig total pressure) and then monitored by HPLC at 1 and 3 hours for the Ligand F and deactivated complex concentrations. The free Ligand F concentration was 0.75, 0.57 and 0.37 weight percent at 0, 1 and 3 hours, respectively, while the deactivated complex concentration was 0.010, 0.57 and 0.89 weight percent at 0, 1 and 3 hours respectively.

EXAMPLE 22

The same procedure as in Example 21 was followed except the catalyst solution was treated with 1 milliliter of 1,3-butadiene and then heated at 145° C. for 3 hours (45 psig total pressure). The free Ligand F concentration measured by HPLC (high pressure liquid chromatography) was 0.75, 0.66, and 0.62 weight percent at 0, 1 and 3 hours, respectively, while the deactivated complex concentration was 0.010, 0.012, and 0.05 weight percent at 0, 1 and 3 hours respectively.

EXAMPLE 23

A catalyst solution was prepared by dissolving 81.1 milligrams of $(TPP)_3Rh(CO)H$ into 29.9 grams of tetraethylene glycol dimethyl ether, which resulted in a rhodium concentration of 300 ppm. TPP is triphenylphosphine. 15 grams of this bright yellow solution was charged to a Fisher Porter bottle under inert gas. To this solution was added 20 psi of butadiene with stirring. The pressure dropped as the butadiene dissolved into the solution. The reactor was repressured twice with butadiene (20 psig) and then the reaction was place under a total of 45 psig with nitrogen. The solution was heated to 120° C. for 15 minutes. No color change was observed and the solution had the appearance of the freshly charged catalyst solution. 1.5 grams of triphenylphosphine was added to the solution, which resulted in a solution containing 275 parts per million rhodium and 9.1 weight percent triphenylphosphine. At ambient temperature, the reaction was placed under vacuum for 4 hours to remove any excess butadiene.

Since the solvent has a very high boiling point, the concentration of rhodium was assumed to have remained unchanged while under vacuum. Indeed, no change in volume was detected visually while under vacuum. 15.0 milliliters of the 275 parts per million solution was charged to a 100 milliliter autoclave. Hydroformylation with 115 psig of an equimolar ratio of propylene, carbon monoxide and hydrogen (1:1:1 at 115 psig) at 100° C. resulted in a rate of 1.4 gmol/L-h (gram moles per liter per hour).

EXAMPLE 24

This example is a control for Example 23. 15 grams of the catalyst solution prepared in Example 23 was charged to a Fisher Porter bottle under inert gas. 45 psig of nitrogen was added to the reaction vessel, then the reaction was heated to 120° C. for 15 minutes. This thermal treatment caused the solution to turn from bright yellow to dark brown. After heating, 1.5 grams of triphenylphosphine was added to the reaction mixture, which resulted in a solution containing 275 parts per million of rhodium and 9.1 weight percent triphenylphosphine. 15.0 milliliters of the 275 parts per million solution was charged to a 100 milliliter autoclave. Hydroformylation at 115 psig with an equimolar ratio of propylene, carbon monoxide and hydrogen (1:1:1 at 115 psig) at 100° C. resulted in a rate of 0.8 gmol/L-h.

EXAMPLE 25

A catalyst solution was prepared by adding 113 milligrams of $(TPP)_3Rh(CO)H$ to 40.4 grams Filmer IBT® available from Union Carbide Corporation, Danbury, Conn., resulting in a rhodium concentration of 312 parts per million. At this point, the rhodium complex was a suspended in the solvent. Approximately 20 grams of this solution of $(TPP)_3Rh(CO)H$ in tetraglyme was charged to a Fisher Porter bottle under inert gas. To this solution was added 30 psi of butadiene with stirring. The pressure dropped to 20 psig as the butadiene dissolved into the solution. The reactor was repressured twice with butadiene (30 psig) and then the pressure was adjusted to 60 psig with nitrogen. The solution was placed into 140° C. oil bath, which caused the reaction to become homogeneous within a minute. The reaction was maintained at 140° C. for 50 minutes. The solution maintained a bright yellow color during the thermal treatment. The reaction vessel was removed from the oil bath and the butadiene was vented from the reactor while the reaction was hot. After gas evolution ceased, the reaction vessel was placed carefully placed under dynamic vacuum until gas evolution had ceased for 10 minutes. The reaction was then placed under a slight positive pressure of nitrogen. The reaction vessel was again heated to 140° C. for 60 minutes, which resulted in no observable color change. Upon cooling to ambient temperature, 10 weight percent of triphenylphosphine was added to the solution, which resulted in a solution containing 284 parts per million rhodium and 9.1 weight percent triphenylphosphine. 15.0 milliliters of the 284 parts per million solution was charged to a 100 milliliter autoclave. Hydroformylation under 95 psig of an equimolar ratio of propylene, carbon monoxide and hydrogen at 100° C. resulted in a rate of 1.0 gmol/L-h.

EXAMPLE 26

This example serves as a control for Example 25. Approximately 20 grams of the solution prepared in Example 25 was charged to a Fisher Porter bottle under inert gas. 60 psig of nitrogen was added to the reaction vessel, then the reaction was heated to 140° C. for approximately 110 minutes. This treatment caused the solution to turn from bright yellow to dark brown. This solution was place into and out of the oil bath at the same time as the solution in Example 25. After thermal treatment, 10 weight percent of triphenylphosphine was added to the reaction mixture. This resulted in a solution containing 284 parts per million of rhodium and 9.1 weight percent triphenylphosphine. 15 milliliters of the 284 parts per million solution was charged to a 100 milliliter autoclave. Hydroformylation under 95 psig of an equimolar ratio of propylene, carbon monoxide and hydrogen at 100° C. resulted in a rate of 0.3 gmol/L-h.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A method of stabilizing a metal-organophosphorus ligand complex catalyst against deactivation in a process which comprises reacting one or more reactants in the presence of a metal-organophosphorus ligand complex catalyst and optionally free organophosphorus ligand to produce a reaction product fluid comprising one or more products, and in which at least a portion of said process is conducted under separation conditions sufficient to effect at least some deactivation of the metal-organophosphorus ligand complex catalyst, which method comprises conducting the portion of said process that occurs under separation conditions in the presence of one or more alkadienes sufficient to prevent and/or lessen deactivation of the metal-organophosphorus ligand complex catalyst.

2. The method of claim 1 comprising stabilizing a metal-organophosphorus ligand complex catalyst against deactivation in a hydroformylation process which comprises reacting one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes, and in which at least a portion of said hydroformylation process is conducted under separation conditions sufficient to effect at least some deactivation of the metal-organophosphorus ligand complex catalyst, which method comprises conducting the portion of said hydroformylation process that occurs under separation conditions in the presence of one or more alkadienes sufficient to prevent and/or lessen deactivation of the metal-organophosphorus ligand complex catalyst.

3. A hydroformylation process which comprises reacting one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes, and in which at least a portion of said hydroformylation process is conducted under separation conditions sufficient to effect at least some deactivation of the metal-organophosphorus ligand complex catalyst, wherein the portion of said hydroformylation process that occurs under separation conditions is conducted in the presence of one or more alkadienes sufficient to prevent and/or lessen deactivation of the metal-organophosphorus ligand complex catalyst.

4. A continuous liquid recycle hydroformylation process which comprises reacting one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes, and in which at least a portion of said process is conducted under separation conditions sufficient to effect at least some deactivation of the metal-organophosphorus ligand complex catalyst, wherein the portion of said hydroformylation process that occurs under separation conditions is conducted in the presence of one or more alkadienes sufficient to prevent and/or lessen deactivation of the metal-organophosphorus ligand complex catalyst.

5. The process of claim 3 comprising an improved hydroformylation process which comprises (i) reacting in at least one reaction zone one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone the one or more aldehydes from said reaction product fluid, and wherein said separation is conducted at a temperature sufficiently high and/or at a carbon monoxide partial pressure sufficiently low to effect at least some deactivation of the metal-organophosphorus ligand complex catalyst, the improvement comprising conducting said separation in the presence of one or more alkadienes sufficient to prevent and/or lessen deactivation of the metal-organophosphorus ligand complex catalyst.

6. The process of claim 4 comprising an improved continuous liquid recycle hydroformylation process which comprises (i) reacting in at least one reaction zone one or more mono-olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone the one or more aldehydes from said reaction product fluid, and wherein said separation is conducted at a temperature sufficiently high and/or a carbon monoxide partial pressure sufficiently low to effect at least some deactivation of the metal-organophosphorus ligand complex catalyst, the improvement comprising conducting said separation in the presence of one or more alkadienes sufficient to prevent and/or lessen deactivation of the metal-organophosphorus ligand complex catalyst.

7. The process of claim 1 which comprises a hydroformylation, hydroacylation (intramolecular and intermolecular), hydroamidation, hydrocyanation, hydroesterification or carbonylation process.

8. The process of claim 5 wherein said separation comprises solvent extraction, crystallization, distillation, vaporization, wiped film evaporation, falling film evaporation, phase separation, filtration and/or membrane separation.

9. The process of claim 1 wherein the one or more alkadienes comprise conjugated diolefins and/or cumulenes.

10. The process of claim 1 wherein the one or more alkadienes undergo complexation with the metal-organophosphorus ligand complex catalyst under separation conditions.

11. The process of claim 1 wherein the one or more alkadienes comprise butadiene, allene and/or isoprene.

12. The process of claim 2 wherein the one or more mono-olefinic unsaturated compounds have 4 or greater carbon atoms.

13. The process of claim 2 wherein the one or more aldehydes have 5 or greater carbon atoms.

14. The process of claim 5 wherein the temperature in said separation zone is from about 10° C. to about 100° C. greater than the temperature in said reaction zone.

15. The process of claim 1 wherein said metal-organophosphorus ligand complex catalyst comprises rhodium complexed with an organophosphorus ligand having the formula selected from:

(i) a triorganophosphine ligand represented by the formula:

wherein $R^1$ is the same or different and represents a substituted or unsubstituted monovalent hydrocarbon radical containing from 1 to 24 carbon atoms or greater;

(ii) a mono-organophosphite represented by the formula:

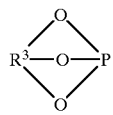

wherein $R^3$ represents a substituted or unsubstituted trivalent hydrocarbon radical containing from 4 to 40 carbon atoms or greater;

(iii) a diorganophosphite represented by the formula:

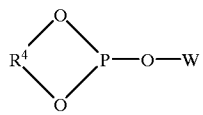

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and represents a substituted or unsubstituted monovalent hydrocarbon radical; and (v) an organopolyphosphite containing two or more tertiary (trivalent) phosphorus atoms represented by the formula:

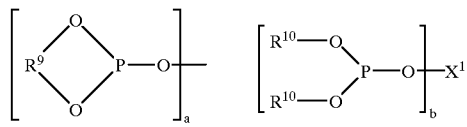

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

16. The process of claim 2 wherein at a temperature sufficiently high and/or a carbon monoxide partial pressure sufficiently low to effect at least some deactivation of the metal-organophosphorus ligand complex catalyst, the one or more alkadienes (i) have a coordination strength with respect to the metal of said metal-organophosphorus ligand complex catalyst sufficient to compete with carbon monoxide to effect at least some coordination with the metal of said metal-organophosphorus ligand complex catalyst, and (ii) have a coordination strength with respect to the metal of said metal-organophosphorus ligand complex catalyst sufficient not to compete with coordination of the organophosphorus ligand with the metal of said metal-organophosphorus ligand complex catalyst.

17. The process of claim 2 wherein at a temperature sufficiently high and/or a carbon monoxide partial pressure sufficiently low to effect at least some deactivation of the metal-organophosphorus ligand complex catalyst the one or more alkadienes (i) have a coordination strength with respect to the metal of said metal-organophosphorus ligand complex catalyst sufficient to effect at least some coordination with the metal of said metal-organophosphorus ligand complex catalyst, and (ii) have a coordination strength with respect to the metal of said metal-organophosphorus ligand complex catalyst less than the organophosphorus ligand of said metal-organophosphorus ligand complex catalyst.

* * * * *